United States Patent [19]

Laurila et al.

[11] Patent Number: 5,776,474
[45] Date of Patent: Jul. 7, 1998

[54] SKIN AND HAIR CARE PRODUCT

[75] Inventors: Maija Laurila, Espoo; Pekka Vapaaoksa, Tampere, both of Finland

[73] Assignee: Carefibres Oy, Espoo, Finland

[21] Appl. No.: 750,002

[22] PCT Filed: Jun. 2, 1995

[86] PCT No.: PCT/FI95/00314

§ 371 Date: Jan. 22, 1997

§ 102(e) Date: Jan. 22, 1997

[87] PCT Pub. No.: WO95/33438

PCT Pub. Date: Dec. 14, 1995

[30] Foreign Application Priority Data

Jun. 2, 1995 [FI] Finland .................. 942609

[51] Int. Cl.$^6$ .................. A61K 6/00
[52] U.S. Cl. .................. 424/401
[58] Field of Search .................. 424/401

[56] References Cited

U.S. PATENT DOCUMENTS 4,786,367 11/1988 Bogart et al. .
5,121,762 6/1992 DiPinto et al. .

FOREIGN PATENT DOCUMENTS

| 28 22 125 | 11/1979 | Germany . |
| 41 29 769 | 3/1993 | Germany . |
| 1064271 | 4/1967 | United Kingdom . |
| WO 93/13249 | 7/1993 | WIPO . |

*Primary Examiner*—Joseph L. Schofer
*Assistant Examiner*—N. Sarofin
*Attorney, Agent, or Firm*—Pollock, Vande Sande & Priddy

[57] ABSTRACT

Skin or hair care product contains an agent acting cosmetically on the hair or skin, for example thioglycolic acid. The product is fibrous material, wherein the cosmetically acting material is absorbed, the absorbed material containing amino groups. A cellulose-based fiber containing polysilicic acid is used as the fibrous material, preferably viscose fiber, and the active agent is bound to the material through the polysilicic acid.

12 Claims, No Drawings

SKIN AND HAIR CARE PRODUCT

FIELD OF THE INVENTION

The present invention relates to a skin and hair care product containing an agent acting cosmetically on hairs or skin, for example thioglycolic acid.

BACKGROUND OF THE INVENTION

Presently many skin and hair care products are known existing in different product forms and being applied to the object to be treated during the use. Thioglycolic acid acting through chemical reduction method is generally used for both waving of hair and straightening of a curly hair. The agent penetrates into the hair structure and brakes cystine (sulphur) bridges which has an essential effect on the shape of the hairs and then enables the setting of the hairs to a new shape. The, most used chemical is the ammonium salt of thioglycolic acid. In addition, other chemical substances are known, such as glycerol monothioglycolate, cysteine, 2- and 3-mercaptopropionic acid, 2mercaptoethylamine and ammonium or sodium sulphite, which all allow to achieve permanent waving of hair through reducing action. (Chemical and Physical Behavior of Human Hair, C.R. Robbins, Van Nostrand Reinhold Company).

The disadvantage of all these is as a rule the unpleasant odour caused by the mercaptans as well as their irritating effect when they occasionally enter the skin or mucous membrane. The skin irritation and odour are in some cases limiting factors to such an extent that people with a sensitive skin and allergy can not at all use cosmetic preparations containing these chemicals.

Further more, the above-mentioned preparations are sold as various liquid mixtures, which increases the transport costs. The use of these preparations requires in addition various dosing and protecting measures during the treatment, and when they are used according to the present practice, they cause additional waste load for example in effluents of hair dressing saloons.

SUMMARY OF THE INVENTION

By means of the present invention the above-mentioned odour disadvantages can be diminished considerably and the use of chemicals can be cut. Further, by means of this new technique excess chemicals can be either destroyed in a controlled manner or regenerated for new use. Moreover, the experiments have shown that the invention speeds up the actual permanent waving operation or any other skin or hair care operation, is more gentle to the hairs and does not much change permanent waving technique.

The product according to the present invention is mainly characterized in that it is of fibrous material having, the cosmetically acting;material absorbed therein, the absorbed material containing amino groups.

According to one advantageous;embodiment the fibrous material is cellulose based fiber containing polysilicic acid, preferably viscose fiber, where the active agent is bound through polysilicic acid.

According to some advantageous embodiments, the active agent is an ammonium salt of a compound,-reducing sulphur bridges of the hair structure, such as ammonium thioglycolate or thiolactate, when the product is used for permanent waving, or the, active agent is ammonium salicylate, when the product is used for the treatment of skin indurations.

DETAILED DESCRIPTION OF THE PREFERRED EMBODIMENTS

According to the present practice the hairdresser often uses a non-woven fabric as support paper when winding the hairs, whereafter the hairs are wet with the permanent waving chemical.

When using the invention, the hairdresser can now replace this non-woven fabric with the material according to the invention containing a ready-to-use agent. The advantage of the use of the material according to the invention is also that the chemical effect on sulphur bridges can be directed more accurately, which makes it possible to avoid unnecessary, skin contact and special, protecting measures. Besides making permanent waving, this is an advantage in the treatment of skin indurations.

The material containing amino groups shall be understood to mean in this context all active agents that contain amine nitrogen either linked covalently or as ammonium cation. Such materials can be especially well absorbed to cellulosic fibers that contain polysilicic acid. For preparing the material according to the invention for skin or hair treatment, it can be impregnated with active agent from a solution where the concentration of the active agent is 1–20 wt.-%, preferably 5 –10 %. Any fiber or blend of fibers can serve as the fibrous structure, cellulosic fiber containing polysilicic acid being, however, preferred, allowing to incorporate the active agent bound through amino groups by a mechanism not known in more detail. For example, when ammonium thioglycolate or thiolactate is used as the active agent for permanent waving, it can be assumed that the fiber containing polysilicic acid offers silanol surface for the exchange of Na ions present in the hair against ammonium ions present in the material, the latter having, been absorbed in the fiber in an excess amount due to the excess amount of ammonia, whereby it opens the hair scales on being released from the fiber and allows the thioglycolate or thiolactate to act.

In case of other fibers the use life of the material will be shortened as the substance volatilizes more easily, because it does not bond so well to other fibers.

In addition to or besides ammonium thioglycolate or thiolactate, the above-mentioned reducing agents can be used in this same way, and salicylic acid and its salts preferably for treatment of skin indurations, for example its ammonium salt. The salicylic textile and fiber structures are well-known as commercial products, but the effect of the material described herein will increase by virtue of the above-mentioned ion exchange between the skin and the material.

The viscose fiber with polysilicic acid suitable for the raw material of the product, sold under trademark "VISIL", can be manufactured by some well-known method, for example that disclosed in GB-patent 1064271. In this method the viscose that contains sodium silicate (waterglass) uniformly distributed therein is spun to an acid spinning bath, in which the regeneration of the viscose to cellulose takes place and at the same time the sodium silicate contained in the viscose is precipitated as polysilicic acid. Also viscose fiber "VISIL-AP" can be used, the manufacturing of which is described in Finnish Patent Application 916187. Thereby the polysilicic acid viscose made by the method according to the GB-patent has been aftertreated with a solution containing aluminium, for example with sodium aluminate solution, whereby aluminium silicate groups improving the retention of the polysilicic acid in the viscose structure are generated.

The amount of the polysilicic acid in viscose fibers, calculated as $Spe_2$, can be 10–40 wt.-% of total: mass of the fiber, and when, aluminium silicate is used, the aluminium content calculated as alumina can: vary between 0.5 wt.-% 15 wt.-% of the total amount of the polysilicic acid containing fiber. The polysilicic ac id has additionally a well-known positive effect on the quality of the hair, and it is possible that also fibers containing polysilicic acid have an advantageous effect in-contact with the hair.

The products can be preserved dry, and when used, the product itself or the object to be treated, such as hairs or skin, is wetted so that the agent can start its effect.

The invention will be described in the following by way of examples, which, however, are not restrictive.

EXAMPLES

Example 1 (preparation of the product)

A material containing "VISIL" non-woven fabric $40g/m^2$ was prepared by impregnating the material with a solution containing ammonia (a 25 %-ic base solution) and thioglycolic acid (a 98 % ic base solution). The non-woven fabric was cut to pieces of approximately 15×5 cm and they were impregnated with the solution just the amount that the liquid did not trickle from the pieces. The liquid was absorbed in this way is about 2.5 ml. The wetted fiber was wound together with the hairs, which had been moistened with water, around a curler used for permanent waving, a food packaging film was wrapped thereon, and the sample: was kept in an incubator, at about 40° C., for 15 –30 min, and the controls at ambient temperature. After the sufficient treatment time the hair were removed from the wrap and they were rinsed with a large volume of water (under running water).

Example 2

A material according to Example 1 was prepared using a solution containing 2.5 % of ammonia and 7.5 % of thioglycolic acid, and the hairs were treated as described in Example 1. Excellent curls were achieved as a result at both treatment temperatures, and the feel of the hairs was better than made in a traditional way. Moreover, the curls were better than those achieved by a corresponding method using a commercial product.

Example 3

A material according to Example 1 was prepared using a solution containing 5 % of ammonia and 5 % thioglycolic acid, and the hairs were treated as described in Example 1. Excellent curls were achieved as a result at both treatment temperatures, and the feel of the hair was better than made in a traditional way.

Example 4

The material according to Example 1 was dried, the hairs were treated as described in Example 1, and in addition to that, after winding the non-woven fabric together with the hairs was wetted before heat treatment. The created curl was not as strong as made with the moist non-woven fabric according to Example 1.

Example 5

A material according to Example 1 was manufactured, containing 80 $g/M^2$ VISIL non-woven fabric, which was impregnated with a solution containing 5% of ammonia and 15% of thioglycolic acid, and the product was dried. The hairs were treated as described in Example 4. Both treatment temperatures resulted in curls which were not as strong as those made with the moist non-woven fabric according to Example 1.

Example 6

A product was prepared from the non-woven fabric material according to Example 1 by impregnating it with a solution containing 2.5 % of ammonia and 7.5 % of salicylic acid. The product can be used for treatment of skin indurations.

Example 7

A material according to Example 1 was prepared, but instead of thioglycolic acid thiolactate (97 %-ic base solution) was -used, and the hairs were treated as described in the Example 1.

Example 8

A material according to Example 3 was prepared by using thiolactate and by treating the hair in the way described in Example 1. Still better feeling and better looking curls were achieved as a result compared with the thioglycolate treatment.

We claim:

1. A skin and hair care product made of water-insoluble cellulose-based fiber that contains polysilicic acid, an active agent acting cosmetically on hairs or skin and containing amino groups absorbed in the water-insoluble cellulose-based fiber, said water-insoluble cellulose-based fiber being of the type containing polysilicic acid already prior to absorbing the active agent, and said active agent being bound to said cellulose-based fiber through the polysilicic acid contained in the fiber.

2. A product according to claim 1, wherein said water-insoluble cellulose-based fiber is viscose fiber.

3. A product according to claim 1, wherein the active agent is an ammonium salt.

4. A product according to claim 3, wherein the active agent is an ammonium salt of a compound reducing sulphur bridges of a hair structure, and wherein the product is for permanent waving.

5. A product according to claim 4, wherein the active agent is an ammonium salt of a reducing thioacid.

6. A product according to claim 5, wherein the ammonium salt of a reducing tyhioacid is selected from a group consisting of ammonium thioglycolate and ammonium thiolactate.

7. A product according to claim 3, wherein the active agent is ammonium salicylate, and wherein the product is for treatment of skin indurations.

8. A product according to claim 1, wherein the product is in the form of a non-woven fabric.

9. A product according to claim 4, wherein the product is in the form of a non-woven fabric.

10. A product according to claim 2, wherein the active agent is an ammonium salt.

11. A product according to claim 2, wherein the product is in the form of a non-woven fabric.

12. A method for carrying out a permanent waving treatment, comprising the steps of:

providing a fabric of cellulose-based fiber containing polysilicic acid, an agent reducing sulphur bridges in a hair structure having been absorbed in said cellulose-based fiber, and said cellulose-based fiber being of the type containing polysilicic acid already prior to absorbing the agent, and placing the fabric in contact with the hair.

* * * * *